(12) United States Patent
Ruppin et al.

(10) Patent No.: US 6,605,743 B1
(45) Date of Patent: Aug. 12, 2003

(54) CONTINUOUS PROCESS FOR THE PREPARATION OF PIVALOYL CHLORIDE AND OF AROYL CHLORIDE

(75) Inventors: Christophe Ruppin, Pierre-Benite (FR); Philippe Corbiere, Survilliers (FR)

(73) Assignee: Elf Atochem S.A., Puteaux (FR)

( * ) Notice: Subject to any disclaimer, the term of this patent is extended or adjusted under 35 U.S.C. 154(b) by 0 days.

(21) Appl. No.: 09/219,450

(22) Filed: Dec. 23, 1998

(30) Foreign Application Priority Data

Dec. 23, 1997 (FR) .............................. 97 16326

(51) Int. Cl.⁷ .................. C07C 65/60; C07C 51/64; C07C 51/58
(52) U.S. Cl. .................. 562/855; 562/856; 562/840; 562/866; 562/861
(58) Field of Search .................. 562/840, 856, 562/866, 861, 855

(56) References Cited

U.S. PATENT DOCUMENTS

| | | | | |
|---|---|---|---|---|
| 1,793,917 A | * | 2/1931 | Faber | 562/840 |
| 1,921,767 A | | 8/1933 | Mills | |
| 1,965,556 A | | 7/1934 | Mills | |
| 2,016,784 A | * | 10/1935 | Krenzlein et al. | 562/840 |
| 3,282,989 A | * | 11/1966 | Renckhoff et al. | 562/840 |
| 3,284,488 A | * | 11/1966 | Renckhoff et al. | 562/840 |
| 3,681,454 A | * | 8/1972 | Rondestvedt, Jr. | 562/855 |
| 3,835,187 A | * | 9/1974 | Dyson | 562/840 |
| 4,163,753 A | | 8/1979 | Pivawer | |

OTHER PUBLICATIONS

Derwent Publications of JP 57 082336.
Derwent Publications of JP 57 165341.
Patent Abstract of Japan, vol. 6, No. 165 (Aug. 28, 1982) of JP 57 082337.

* cited by examiner

Primary Examiner—Alan L. Rotman
Assistant Examiner—Taylor V. Oh
(74) Attorney, Agent, or Firm—Millen, White, Zelano & Branigan, P.C.

(57) ABSTRACT

The invention relates to a continuous process for the preparation of pivaloyl chloride and of aroyl chloride, in particular of benzoyl chloride, which consists in reacting pivalic acid with a trichloromethylated aromatic compound in the presence of a catalyst at a temperature of between 60° C. and 180° C. under reduced pressure. The products formed are continuously removed from the reaction region, the hydrogen chloride formed being treated in a washing region in which a trichloromethylated compound moves countercurrentwise.

18 Claims, No Drawings

CONTINUOUS PROCESS FOR THE PREPARATION OF PIVALOYL CHLORIDE AND OF AROYL CHLORIDE

The invention relates to a continuous process for the preparation of pivaloyl chloride and of aroyl chloride, in particular of benzoyl chloride.

Pivaloyl chloride is an important synthetic intermediate in the chemical industry. It is very widely used in the synthesis of various pharmaceutical products (antiviral agents, anti-inflammatory agents) or plant-protection products (herbicides, insecticides). It is also used in the synthesis of peresters, such as tert-butyl perpivalate and tert-amyl perpivalate, which are used in particular as initiators in radical polymerization. Aroyl chlorides are also important synthetic intermediates, used in particular in the manufacture of peroxides and peresters and in the synthesis of various colorants, insecticides or rubber additives.

The main access routes to pivaloyl chloride comprise processes in which conventional reagents, such as phosgene, sulphonyl chloride, phosphorus tri- or pentachlorides, thionyl chloride or oxalyl chloride, are reacted with pivalic acid or alternatively in which carbon monoxide is reacted, in the presence of a catalyst, with tert-butyl chloride.

However, all these processes represent complex technologies, on account of the reagents involved and the need to carry out expensive treatments of the products obtained and of the effluents, which rule out industrial production.

Thus, for example in the process described by Butlerow (Justus Liebigs Ann. Chem., p. 373, 1874), which consists in reacting pivalic acid with phosphorus pentachloride according to the reaction:

$$(CH_3)_3COOH + PCl_5 \rightarrow (CH_3)_3CCOCl + POCl_3 + HCl$$

the $POCl_3$ and the pivaloyl chloride obtained have boiling temperatures which are so close (104–106° C.) that it is virtually impossible to separate them. This author also added potassium pivalate to the reaction mixture obtained, in order to convert $POCl_3$ to $P_2O_5$ according to the reaction:

$$3(CH_3)_3CCO_2K + 2POCl_3 \rightarrow 3(CH_3)_3CCOCl + P_2O_5 + 3KCl$$

Other authors (Bull. Soc. Chim. Fr., p. 350–351, 1939), in the light of this process, have proposed to prepare pivaloyl chloride directly in a single stage by reaction of sodium pivalate with $POCl_3$ according to the reaction:

$$3(CH_3)_3CCO_2Na + 2POCl_3 \rightarrow 3(CH_3)_3CCOCl + P_2O_5 + 3NaCl$$

With a 25% molar excess of sodium pivalate, the molar yield of pivaloyl chloride is only 81% with respect to the $POCl_3$ employed, which, of course, rules out an industrial process, all the more so since the price of sodium pivalate is much higher than the price of the desired pivaloyl chloride.

The proposal has been made to use phosphorus trichloride in place of $PCl_5$ (J. Am. Chem. Soc., 54, p. 3438–41, 1932) according to the reaction:

$$PCl_3 + (CH_3)_3CCOOH \rightarrow (CH_3)_3CCOCl + H_3PO_3 + HCl$$

The hydrochloric acid formed is continuously removed and the pivaloyl chloride is purified by distillation after separation by settling of the phosphorous acid, which can be recovered in value. However, the molar yield of pivaloyl chloride is less than 90% with respect to the pivalic acid employed and it is very difficult to remove the final traces of phosphorous acid (reducing product), which traces rule out the use of pivaloyl chloride in certain syntheses.

One of the most frequently mentioned processes for the synthesis of pivaloyl chloride in the literature is that employing thionyl chloride according to the reaction:

$$(CH_3)_3CCOOH + SOCl_2 \rightarrow (CH_3)_3CCOCl + SO_2 + HCl$$

The reaction is generally carried out in the presence of a 20% to 50% molar excess of $SOCl_2$.

According to these conditions, molar yields of distilled pivaloyl chloride are obtained which are close to 90%. The addition of catalysts, such as DMF, pyridine or N-methylacetamide, makes it possible to increase the reaction kinetics and to improve the selectivity (fall in the percentage of by-products, such as the anhydride).

However, this process has the disadvantage of resulting in a pivaloyl chloride which can comprise sulphur. In addition, in the eventuality of the use of a catalyst, the catalyst is difficult to recycle.

Pivaloyl chloride can also be obtained from phosgene according to the reaction:

$$(CH_3)_3CCO_2H + COCl_2 \rightarrow (CH_3)_3CCOCl + HCl + CO_2$$

or alternatively by carbonylation of tert-butyl chloride in the presence of catalysts, such as $AlCl_3$ or $FeCl_3$, according to the reaction:

$$(CH_3)_3CCl + CO \rightarrow (CH_3)_3COCl$$

However, these processes exhibit the disadvantage of using highly toxic reagents which are difficult to handle and requiring the use of catalysts in order to obtain a good selectivity and yields of greater than 90%.

It should be noted that, in the case of the carbonylation of tert-butyl chloride, the use of catalysts is capable of resulting in the formation of impurities or of causing the retrogression of the product formed.

The access routes to aroyl chlorides, in particular to benzoyl chloride, also comprise processes in which conventional reagents, such as $PCl_5$, $COCl_2$ or $SOCl_2$, are reacted with aromatic acids.

More specifically, benzoyl chloride is obtained industrially by partial hydrolysis of phenylchloroform according to the reaction:

$$C_6H_5CCl_3 + H_2O \rightarrow C_6H_5COCl + 2HCl$$

or by reaction of benzoic acid with phenylchloroform according to the reaction:

$$C_6H_5CCl_3 + C_6H_5CO_2H \rightarrow 2C_6H_5COCl + HCl$$

The simultaneous production of pivaloyl chloride and of aroyl chloride, more specifically of benzoyl chloride, is not described to any great extent in the literature.

This simultaneous production of acid chlorides is based on the reaction:

$$RCOOH + C_6H_5CCl_3 \rightarrow RCOCl + C_6H_5COCl + HCl$$

which is a chlorodehydroxylation reaction of RCOOH by $C_6H_5CCl_3$.

Thus, in Patent JP 86-021 617 B, a process for the batchwise preparation of pivaloyl chloride and of benzoyl chloride is disclosed.

This process consists in reacting, in a first stage, pivalic acid and phenylchloroform in a stoichiometric amount at atmospheric pressure in the presence of $FeCl_3$ at a temperature ranging from 40° C. to 150° C. and then, after removal of the HCl formed, in distilling the pivaloyl chloride under reduced pressure. Subsequently, in a second stage, after introduction of a fresh charge of catalyst, the reaction mixture is heated to a temperature of between 40° and 160° C. and then the benzoyl chloride formed is distilled under reduced pressure.

Although this process makes it possible to obtain acceptable yields, of between 90% and 95%, of pivaloyl chloride and of benzoyl chloride, there are a number of disadvantages to this way of operating.

Thus, it is necessary to remove all the pivaloyl chloride before carrying out the second stage, at the risk of decarbonylating the pivaloyl chloride according to the reaction:

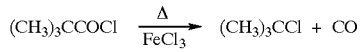

In order to avoid this, the authors of the patent mentioned completed the distillation by extracting the residual pivaloyl chloride by partial distillation under reduced pressure of the benzoyl chloride formed. Under these conditions, the distillating fraction is composed essentially of benzoyl chloride, with a few % of pivaloyl chloride and of other unidentified compounds.

There is a significant disadvantage to this way of operating, when it is known that various by-products are capable of being formed as a result of side reactions, the most important of which are the following:

an equilibrium transhalogenation reaction between benzoyl chloride and pivalic acid:

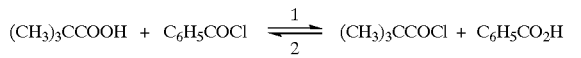

the reaction of the benzoic acid formed with benzoyl chloride, to result in benzoic anhydride:

$$C_6H_5CO_2H + C_6H_5COCl \rightarrow (C_6H_5CO)_2O + HCl$$

These by-products formed during the first stage are difficult to avoid. The authors of the patent mentioned also, in the second stage, added a significant amount of $FeCl_3$ in order to convert the by-products and in particular benzoic anhydride in the presence of unconverted $C_6H_5CCl_3$ according to the reaction:

$$(C_6H_5CO)_2O + C_6H_5CCl_3 \rightarrow 3C_6H_5COCl$$

Finally, this batch process exhibits lengthy, successive, transitory and not very productive operations. In addition, this process is completely silent with regard to any recovery in value of the hydrochloric acid formed.

The Applicant Company has now found a continuous process for the preparation of pivaloyl chloride and of aroyl chloride (2) by reaction of pivalic acid with a trichloromethylated aromatic compound (1) according to the reaction:

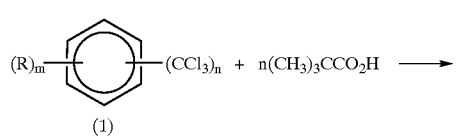

-continued

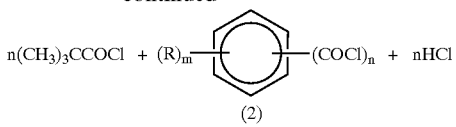

in which R represents a halogen atom, such as F, Cl or Br, a linear or branched alkyl radical having a carbon number ranging from 1 to 4, a linear or branched perfluoroalkyl radical having a carbon number ranging from 1 to 4 or a —COCl radical, m=0, 1 or 2 and n=1, 2 or 3 and in which the —$CCl_3$ groups are situated on non-adjacent carbon atoms when n>1, in the presence of at least one catalyst of Friedel-Crafts type, the said process being characterized in that it consists:

in simultaneously and continuously introducing pivalic acid, at least one trichloro-methylated aromatic compound (1) and at least one catalyst of Friedel-Crafts type into a reaction region and in reacting them with stirring and under reduced pressure at a temperature of between 60° C. and 180° C. and preferably of between 120° C. and 150° C.

in continuously separating the unconverted reactants from the products formed of the gas flow exiting at the top of the reaction region, in partially condensing the said products formed into a liquid mixture comprising pivaloyl chloride and aroyl chloride (2), in treating, in a washing region in which a trichloromethylated aromatic compound (1) moves countercurrentwise, the remaining uncondensed gaseous mixture comprising hydrogen chloride, and in continuously extracting, at the bottom of the said reaction region, a liquid mixture mainly comprising the aroyl chloride (2) formed and the catalyst used in the reaction region, the said mixture being treated in a so-called "reactive" distillation region, from which is extracted, at the top, the aroyl chloride (2).

The unconverted reactants advantageously return to the reaction region.

According to the present invention, the trichloromethylated aromatic compound (1) used in the washing region can be partially or completely introduced into the reaction region after having been used in the washing region. It will preferably be completely introduced into the reaction region, so as advantageously to recycle the pivaloyl chloride absorbed by the trichloromethylated aromatic compound (1) in the washing region.

According to the present invention, the mixture extracted at the bottom of the reaction region, mainly comprising aroyl chloride and also unconverted trichloromethylated aromatic compound (1), catalyst, aroyl anhydride and, optionally, small amounts of by-products, is treated in a so-called "reactive" distillation region under reduced pressure at a temperature at least equal to 120° C. In addition, it is possible to use an additional amount of catalyst of Friedel-Crafts type which is identical to or different from that used in the reaction region. The complementary part of the aroyl chloride formed in the process is recovered at the top. Heavy products are recovered at the bottom and are destroyed, in particular by incineration.

The reaction (1) is carried out with a molar ratio:

$$\frac{\text{trichloromethylated aromatic compound (1)}}{\text{pivalic acid}}$$

ranging from 0.90 n to 1.10 n and preferably of between 1 n and 1.03 n.

According to the present invention, the reaction is carried out in the reaction region under a reduced pressure at most equal to 500 mbar and preferably of between 100 mbar and 400 mbar.

Catalyst of Friedel-Crafts type now denotes a Lewis acid or a Brönsted acid.

Mention will be made, by way of illustration of Lewis acid which can be used according to the invention, of $FeCl_3$, $ZnCl_2$, $SnCl_4$, $AlCl_3$, $SbCl_5$, $CoCl_2$, $BF_3$, and the like.

Use will preferably be made of $FeCl_3$.

Mention will be made, by way of illustration of Brönsted acid which can be used according to the present invention, of sulphuric acid, phosphoric acid, polyphosphoric acids, pyrosulphuric acid, fluoro-sulphonic acid or chlorosulphonic acid. Use will preferably be made of sulphuric acid.

These catalysts of Friedel-Crafts type can be introduced into the reaction region as such or in the form of aqueous solutions or in solution in one of the reactants or else in solution in pivaloyl chloride or aroyl chloride.

According to the present invention, use will be made of a molar amount of pure Lewis acid of between 0.01% and 1% and preferably of between 0.05% and 0.2%, with respect to the amount of pivalic acid employed.

According to the present invention, use will be made of a molar amount of pure Brönsted acid of between 0.1% and 5% and preferably of between 0.05% and 2%, with respect to the amount of pivalic acid employed.

It would not be departing from the scope of the invention if the trichloromethylated aromatic compound moving countercurrentwise in the washing region were different from that introduced into the reaction region.

The pure hydrogen chloride exiting at the top of the said washing region is subsequently advantageously absorbed in water in order to result in commercial aqueous HCl solutions.

The liquid mixture extracted at the top of the reaction region, composed of a mixture of pivaloyl chloride and of aroyl chloride, is advantageously subjected to a distillation under reduced pressure which makes it possible to separate the various chlorides formed.

Mention will be made, by way of illustration of trichloromethylated aromatic compounds (1) which can be used according to the present invention, of:
trichloromethylbenzene or phenylchloroform,
2-chloro-, 3-chloro- and 4-chloro-1-trichloromethylbenzenes,
1,3- and 1,4-bis(trichloromethyl)benzenes,
4-fluoro-1-trichloromethylbenzene,
3,4-dichloro-1-trichloromethylbenzene,
4-trifluoromethyl-1-trichloromethylbenzene.

The process of the invention applies very particularly to the preparation of pivaloyl chloride and of benzoyl chloride from pivalic acid and phenylchloroform.

The process exhibits the advantage of resulting in acid chlorides of high purity and of unchanging quality with high yields of greater than 96%, complete conversion of the reactants and high productivity. In addition, the hydrogen chloride formed is directly recovered in value.

This process also exhibits the advantage of generating few by-products and in particular does not produce gaseous effluents.

The example which follows illustrates the invention.

130 kg/h of pivalic acid, with 0.5 kg/h of a 40% by weight aqueous $FeCl_3$ solution and 285.5 kg/h of a phenylchloroform flow comprising 35.5 kg/h of pivaloyl chloride, are continuously introduced, with stirring and under a pressure of 133 mbar, into a 2.5 m³ glass-lined reactor maintained at 135° C., under stabilized conditions, comprising a mixture comprising benzoyl chloride, phenylchloroform and benzoic anhydride.

Under these conditions, the pivaloyl chloride is immediately formed and evaporated, as well as a portion of the benzoyl chloride.

The gaseous reaction products are continuously extracted at the top of the reactor and are carried into a small separating column equipped with a structured packing of 6 theoretical plates, where they are separated from the unconverted reactants. The unconverted reactants return to the reactor.

After condensation of the mixture of gaseous products, extraction is continuously carried out of, on the one hand, a liquid mixture composed of 147.7 kg/h of pivaloyl chloride, of 82.8 kg/h of benzoyl chloride and of 0.9 kg/h of tert-butyl chloride, which is conveyed to a storage tank in order to be subsequently subjected to a distillation which makes it possible to recover pivaloyl chloride having a purity of greater than 99.5%, and, on the other hand, a gas flow composed of 47.8 kg/h of hydrogen chloride (HCl gas), of 35.6 kg/h of pivaloyl chloride and of 2.7 kg/h of tert-butyl chloride, which is evacuated by a liquid ejector and conveyed into a washing column packed with 9 theoretical plates, in which column the hydrogen chloride is washed countercurrentwise with 200 kg/h of phenylchloroform at 10° C.

47.5 kg/h of HCl gas are recovered at the top of this washing column and are conveyed over a falling film isothermal absorber, where they are absorbed by 95.5 kg/h of water to form 144.9 kg/h of a 33% by weight aqueous HCl solution.

At the bottom of the washing region, the phenylchloroform, which has absorbed the organic compounds present in the gas flow introduced into the said washing column, is conveyed into the reactor; it forms a portion of the 285.6 kg/h of phenylchloroform employed.

At the reactor bottom, 102.3 kg/h of a liquid mixture are continuously extracted, which mixture comprises 55.6 kg of benzoyl chloride,
16.9 kg of phenylchloroform,
21.3 kg of benzoic anhydride,
25 2.8 kg of pivaloyl chloride,
1.4 kg of benzoic acid, catalyst and heavy residues related to the impurities in the phenyl-chloroform employed.

This liquid mixture is discharged into a storage tank and is then subjected to a reactive distillation, in a column with 20 theoretical plates, under reduced pressure at a temperature of between 120° C. and 150° C. and in the presence of 0.1% by weight of $FeCl_3$ with respect to the weight of the mixture. The residual pivaloyl chloride and then benzoyl chloride with a purity of greater than 99.9% emerge at the top of this column.

The heavy products are removed by incineration.

After the distillation operations, the pivaloyl chloride and benzoyl chloride yields are greater than 96.8% and 97% respectively. The hydrochloric acid obtained in this process is a 33% aqueous HCl solution of commercial grade.

The entire disclosure of all applications, patents and publications, cited above and below, and of corresponding French application No. 97/16326, filed Dec. 23, 1997 is hereby incorporated by reference.

What is claimed is:

1. A continuous process for the preparation of pivaloyl chloride and of aroyl chloride (2) by reaction of pivalic-acid with a trichloromethylated aromatic compound (1) according to the reaction:

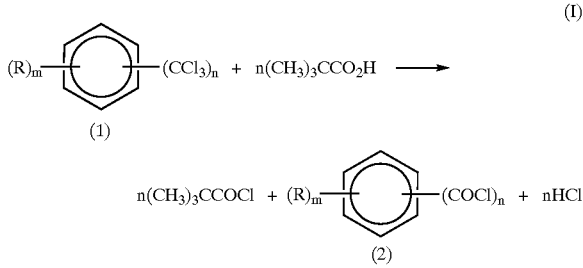

in which R represents a halogen atom, a linear or branched alkyl radical having a carbon number of 1 to 4, a linear or branched perfluoroalkyl radical having a carbon number of 1 to 4 or a —COCl radical, m=0, 1 or 2 and n=1, 2 or 3 and in which the —CCl$_3$ groups are situated on non-adjacent carbon atoms when n>1, in the presence of at least one Friedel-Crafts catalyst, said process comprising simultaneously and continuously introducing pivalic acid, at least one trichloromethylated aromatic compound (1) and at least one Friedel-Crafts catalyst into a reactor and reacting with stirring and under reduced pressure at a temperature of 60° C. to 180° C., continuously separating unconverted reactants from products formed in gas flow exiting at the top of the reaction region, partially condensing the products formed into a liquid mixture comprising pivaloyl chloride and aroyl chloride (2), treating, in a washing region in which a trichloromethylated aromatic compound (1) moves countercurrentwise, remaining uncondensed gaseous mixture comprising hydrogen chloride, and continuously extracting, at the bottom of the said reaction region, a liquid mixture mainly comprising the aroyl chloride (2) formed and the catalyst used in the reaction region, said mixture being treated in a reactive distillation region, from which is extracted, at the top, the aroyl chloride (2).

2. The process according to claim 1, wherein reactive distillation is carried out in the presence of an additional amount of Friedel-Crafts catalyst.

3. The process according to claim 1, wherein the temperature in the reaction region is 120° C. to 150° C.

4. The process according to claim 1, wherein the reaction is carried out in the reactor under reduced pressure at most equal to 500 mbar.

5. The process according to claim 4, wherein the reaction is carried out in the reactor under reduced pressure of 100 mbar to 400 mbar.

6. The process according to claim 1, wherein the reaction (I) is carried out with a molar ratio:

$$\frac{\text{trichloromethylated aromatic compound (1)}}{\text{pivalic}}$$

of 0.90 n to 1.10 n.

7. The process according to claim 1, wherein the Friedel-Crafts catalyst is a Lewis acid.

8. The process according to claim 7, wherein the Lewis acid is FeCl$_3$.

9. The process according to claim 7, wherein a molar amount of Lewis acid of 0.01% to 1%, with respect to the amount of pivalic acid employed, is used.

10. The process according to claim 1, wherein the Friedel-Crafts catalyst is a Brönsted acid.

11. The process according to claim 10, wherein the Brönsted acid is sulphuric acid.

12. The process according to claim 10, wherein a molar amount of Brönsted acid of 0.1% to 5% with respect to the amount of pivalic acid employed, is used.

13. The process according to claim 1, wherein the trichloromethylated compound (1) used in the washing region is completely introduced into the reactor.

14. The process according to claim 1, wherein the trichloromethylated aromatic compound (1) is trichloromethylbenzene.

15. The process according to claim 1, wherein the reaction (I) is carried out with a molar ratio:

$$\frac{\text{trichloromethylated aromatic compound (1)}}{\text{pivalic}}$$

of 1 n to 1.03 n.

16. The process according to claim 7, wherein a molar amount of Lewis acid of 0.05% to 0.2%, with respect to the amount of pivalic acid employed, is used.

17. The process according to claim 1, wherein the trichloromethylated aromatic compound (1) is phenylchloroform.

18. A continuous process for the preparation of pivaloyl chloride and aroyl chloride, comprising simultaneously and continuously reacting pivalic acid and at least one trichloromethylated aromatic compound in the presence of a Friedel-Crafts catalyst, and continuously separating unconverted reactants and a mixture of pivaloyl chloride and aroyl chloride under reduced pressure, wherein the trichloromethylated aromatic compound has formula (1)

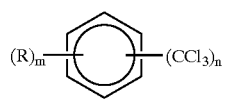

and the aroyl chloride has formula (2)

in which R represents a halogen atom, a linear or branched alkyl radical having a carbon number of 1 to 4, a linear or branched perfluoroalkyl radical having a carbon number of 1 to 4 or a —COCl radical, m=0, 1 or 2 and n=1, 2 or 3 and in which the —CCl$_3$ groups are situated on non-adjacent carbon atoms when n>1.

* * * * *

UNITED STATES PATENT AND TRADEMARK OFFICE
CERTIFICATE OF CORRECTION

| | |
|---|---|
| PATENT NO. | : 6,605,743 B1 |
| APPLICATION NO. | : 09/219450 |
| DATED | : August 12, 2003 |
| INVENTOR(S) | : Christophe Ruppin et al. |

It is certified that error appears in the above-identified patent and that said Letters Patent is hereby corrected as shown below:

Column 7, line 3, "pivalic-acid" should read --pivalic acid--.
Column 7, line 64, "pivalic" should read --pivalic acid--.
Column 8, lines 9 and 10, "wherein the Br önstead" should read --wherein the Brönstead--.
Column 8, line 15, "compound" should read --aromatic compound--.
Column 8, line 26, "pivalic" should read --pivalic acid--.

Signed and Sealed this

Twenty-fourth Day of October, 2006

JON W. DUDAS
*Director of the United States Patent and Trademark Office*